US008900258B2

(12) United States Patent
Tjelmeland

(10) Patent No.: US 8,900,258 B2
(45) Date of Patent: Dec. 2, 2014

(54) DEBRIDEMENT DEVICE

(76) Inventor: Kelly Tjelmeland, Austin, TX (US)

( * ) Notice: Subject to any disclaimer, the term of this patent is extended or adjusted under 35 U.S.C. 154(b) by 1035 days.

(21) Appl. No.: 11/762,862

(22) Filed: Jun. 14, 2007

(65) Prior Publication Data

US 2007/0289145 A1     Dec. 20, 2007

Related U.S. Application Data

(60) Provisional application No. 60/804,946, filed on Jun. 16, 2006.

(51) Int. Cl.
A61B 17/32      (2006.01)
A61B 17/3213    (2006.01)
A61B 17/00      (2006.01)

(52) U.S. Cl.
CPC ... *A61B 17/3213* (2013.01); *A61B 2017/00424* (2013.01); *A61B 2017/320008* (2013.01)

USPC .......................................................... 606/167

(58) Field of Classification Search
USPC .................................. 606/167, 160; 623/6.12
See application file for complete search history.

(56) References Cited

U.S. PATENT DOCUMENTS

| 1,452,930 | A | * | 4/1923 | Polk ................................ 30/356 |
| 3,913,226 | A | * | 10/1975 | Lovato et al. ................ 30/123.5 |
| 4,198,751 | A | * | 4/1980 | Egbert ............................ 30/286 |
| 4,970,786 | A | * | 11/1990 | Harper ......................... 30/123.7 |
| 7,468,042 | B2 | * | 12/2008 | Turovskiy et al. ............ 600/564 |

* cited by examiner

*Primary Examiner* — Jonathan W Miles
(74) *Attorney, Agent, or Firm* — DuBois, Bryant & Campbell LLP; William D. Wiese

(57) ABSTRACT

The preferred embodiment of this invention will allow a medical practitioner to more easily, quickly, and specifically remove unwanted tissue from a patient. The curved blade with a specialized surface for cutting and scraping is better suited than current options for performing this task.

18 Claims, 5 Drawing Sheets

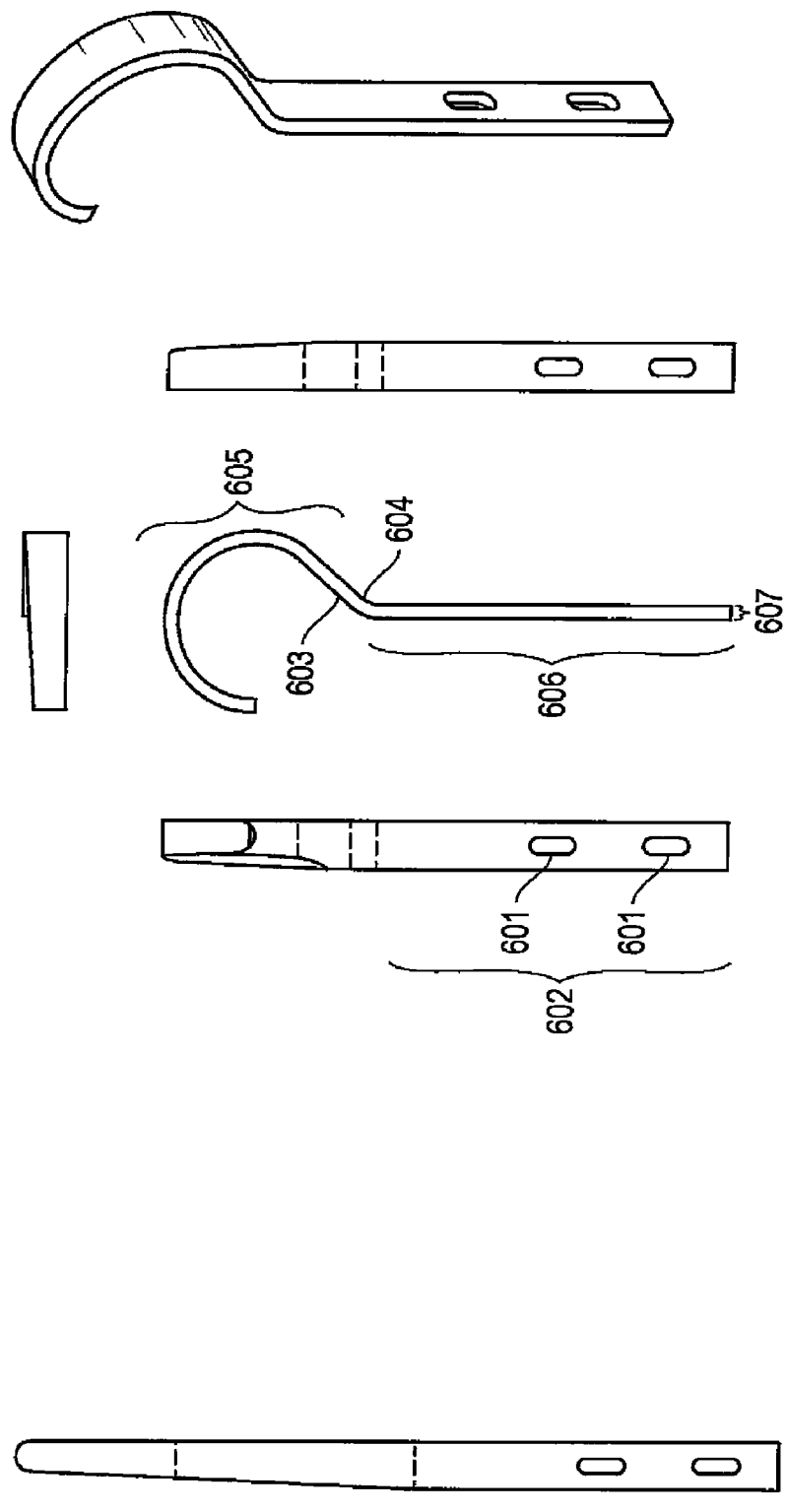

US 8,900,258 B2

DEBRIDEMENT DEVICE

CROSS-REFERENCE TO RELATED APPLICATIONS

This non-provisional application claims priority based upon prior U.S. Provisional Patent Application Ser. No. 60/804946 filed Jun. 16, 2006 in the name of Kelly Tjelmeland, entitled "Debridement Device," the disclosure of which is incorporated herein by reference.

BACKGROUND OF THE INVENTION

1. Technical Field

The present invention relates generally to a device for removing unwanted tissue, and more particularly to a device specialized to cut and scrape dead tissue from wounds underneath a layer of skin.

2. Background

Wounds and surgery areas often contain dead, weakened, contaminated or otherwise unwanted tissue. Such tissue may also be difficult to directly access depending on where the tissue is located relative to a wound or surgery area and relative to healthy tissue. Current options for removing unwanted tissue involve using standard medical devices, such as a standard scalpel, to cut away the unwanted tissue. These options, however, often involve the use of a tool that is not designed specifically for removing unwanted tissue. Consequently, the current options yield less than optimal results and can be more time consuming than necessary. These and other problems are generally solved or circumvented, and technical advantages are generally achieved, by embodiments of the present invention.

BRIEF SUMMARY OF THE INVENTION

In one embodiment of the present invention, the distal end of a blade is curved in a manner such that one face of the blade forms the inner curve of the blade and the other face of the blade forms the outer curve of the blade. At least a portion of one edge of the blade is sharpened. An advantage of the present invention is the specialized shape of the device. The proximal end of a blade may also be connected to an elongated handle. The device of the present invention can be used to remove dead tissue from a wound with less chance for live tissue to be removed.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended clams.

BRIEF DESCRIPTION OF THE DRAWINGS

For a more complete understanding of the present invention, and the advantages thereof, reference is now made to the following descriptions taken in conjunction with the accompanying drawings, in which:

FIG. 5 is a view of a flat pattern of another embodiment of the blade portion of the device of the present invention.

FIG. 6 is a multi-perspective view of another embodiment of the blade portion of the device of the present invention.

DETAILED DESCRIPTION

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention. The present invention will be described with respect to preferred embodiments in a specific context, namely as a device for the debridement of wounds. The invention may also be applied, however, to other situations where removing tissue is desirable.

Figure 1:
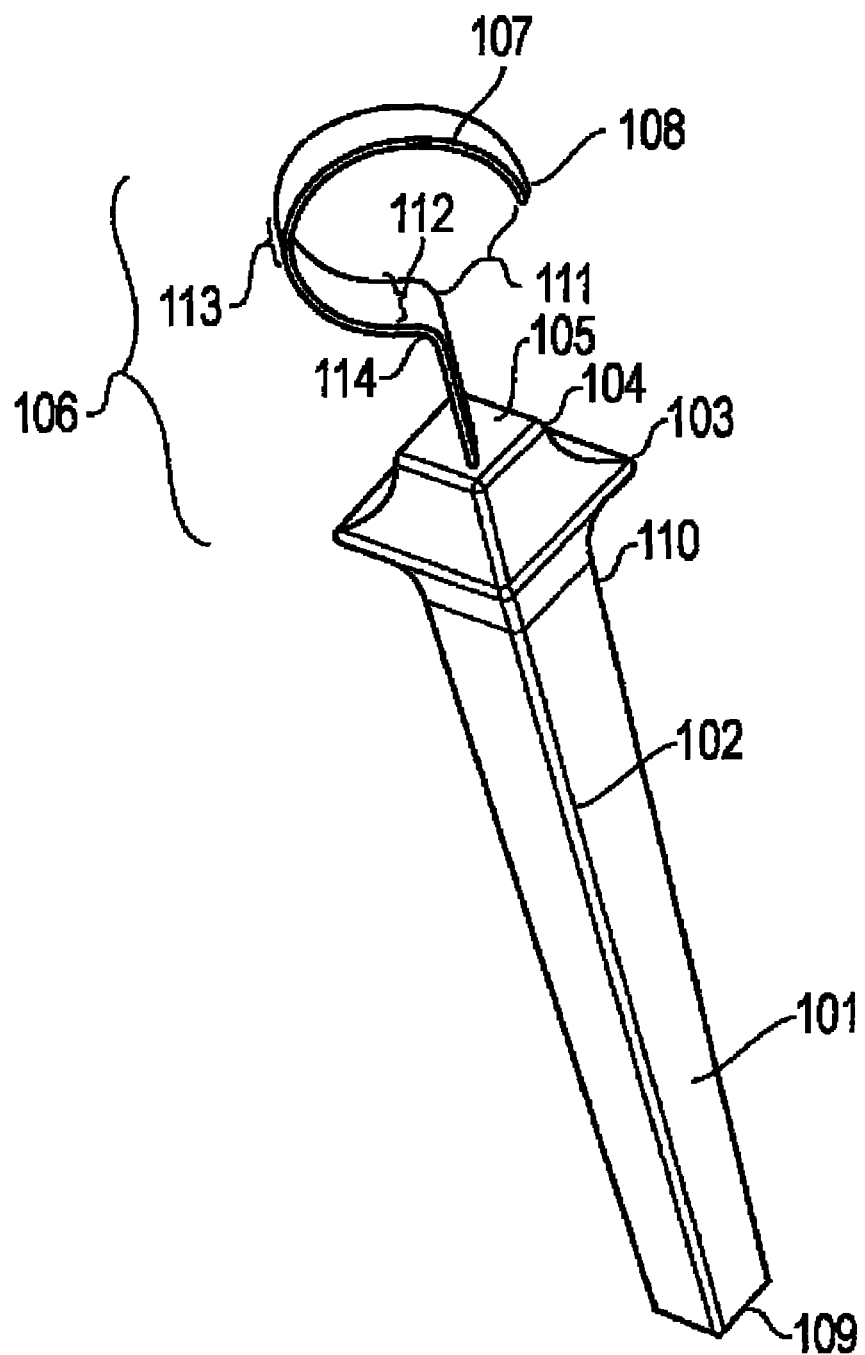
FIG. 1 is a perspective view of one embodiment of the device of the present invention.

With reference now to FIG. 1, a perspective view of the device of the present invention is shown. The device includes a handle 101 and a blade 106 that tapers and curves. The device may also include a guard 103. In one embodiment, the blade 106 is made from a material, typically a metal such as stainless steel, strong enough to be rigid under the conditions of use. The handle 101 and guard 103 are shown using a different material than the blade 106, typically a plastic constructed with an appropriate grip 102. The handle 101, the guard 103, and the blade 106 can be a one piece construction or they can include two or more materials to improve the grip and manipulation of the instrument. From this view, the device has a blade 106 located at the distal end of the device 108 and a handle 101 located at the proximal end of the device 109. A guard 103 is located at the distal end of the handle 110 and the proximal portion of the blade 105.

The blade 106 is configured so that the proximal portion of the blade 105 adjoins, or is integrated into, the guard 103 and the distal end of the handle 110. For example, the handle can be insert molded onto the proximal portion of the blade 105. The proximal portion of the blade 105 serves to affix the blade 106 to the guard 103 and handle 101 and separates the distal portion of the blade 111 from the guard 103 and handle 101. The distal portion of the blade 111 is curved in a manner such that one face of the blade forms the inner curve 112 of the distal portion of the blade 111 and the other face of the blade forms the outer curve 113 of the distal portion of the blade 111. In this embodiment, a junction 114 is located between the curved distal portion of the blade 111 and the straight proximal end of the blade 105. The junction 114 curves in a direction that is opposite of the direction of curvature of the curved distal portion of the blade 111. For instance, the face of the blade that forms the outer curve 113 of distal portion of the blade 111 forms the inner curve of the junction 114. Similarly, the face of the blade that forms the inner curve 112 of distal portion of the blade 111 forms the outer curve of the junction 114. The guard 103 at the distal end of the handle 110 prevents a hand gripping the handle 101 from slipping onto the blade 106 if the hand loses its firm grip on the handle 101. The guard 103 also reduces the risk that a hand gripping the handle 101 will be exposed to tissue or fluids located on or in the area of the blade 106. In one embodiment, the distal portion of the blade 111 is curved into a shape approximating three-fourths of a circle. At least, one edge of the blade 107 is sharpened sufficiently to cut tissue. The sharpened edge 107 can start at the distal end of the blade 108 and continue to the point at which the proximal end of the blade 105 abuts the distal end of the guard 104. Alternatively, only the edge of the curved portion of the blade 111 may be sharpened.

Figure 2:
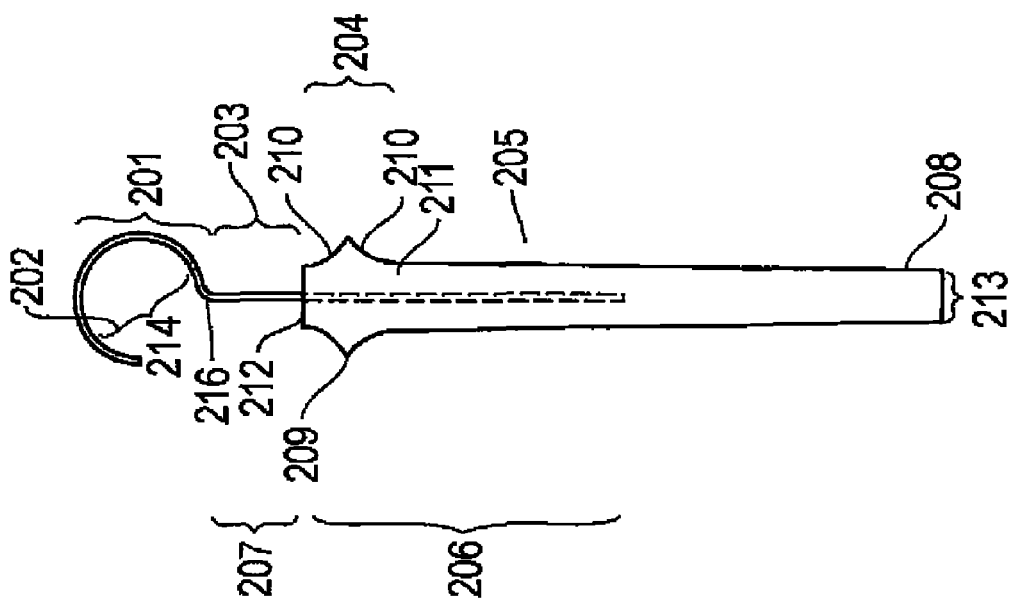
FIG. 2 is a view of one embodiment of the device of the present invention with the face of the blade that forms the inner curve of the blade facing to the side of the page.

With reference now to FIG. 2, a view of one embodiment of the device of the present invention with the inner curve of the blade 214 facing to the side is shown. From this view the curvature of the distal portion of the blade 201 can be seen. In this embodiment the curvature has a radius of 25 millimeters 202. The junction 216 between the curved distal portion of the blade 201 and the straight proximal portion of the blade 203 curves with a radius of 2.5 millimeters. Blades with different curvatures at the distal portion and the junction can be used in order to optimize the device for specific procedures. The straight proximal portion of the blade 203 abuts the guard 204 at the distal end of the handle 205 and extends into the guard and handle a distance of 65 millimeters 206. The straight proximal portion of the blade 207 also extends above the guard a length of 20 millimeters before the blade begins to curve. The guard 204 at the distal end of the handle 205 is shown to extend in a direction perpendicular to the longitudinal axis of the handle 208. The widest point of the guard is located 9.2 millimeters from the distal end of the handle 205 and 20.8 millimeters from the proximal end of the handle 208. The width of the guard at its widest point 209 is approximately three times the width of the handle. Concave surfaces 210 extend from the widest point of the guard 209 to both the proximal end 211 and the distal end 212 of the guard. The width of the handle 213 is 9.75 millimeters at the proximal end of the handle 208.

Figure 3:
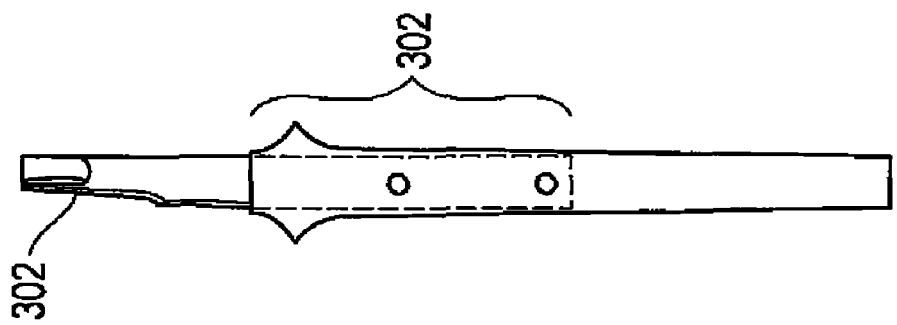
FIG. 3 is a view of one embodiment of the device of the present invention with face of the blade that forms the inner curve of the blade facing forward.

With reference now to FIG. 3, a view of an embodiment of the device of the present invention with the inner curve of the blade facing forward is shown. From this view, the sharpened edge of the tool 301 that is used for cutting and scraping is also shown. The length and sharpness of the sharpened edge can also vary. The proximal portion of the blade 302 is also shown extending into the handle.

Figure 4:
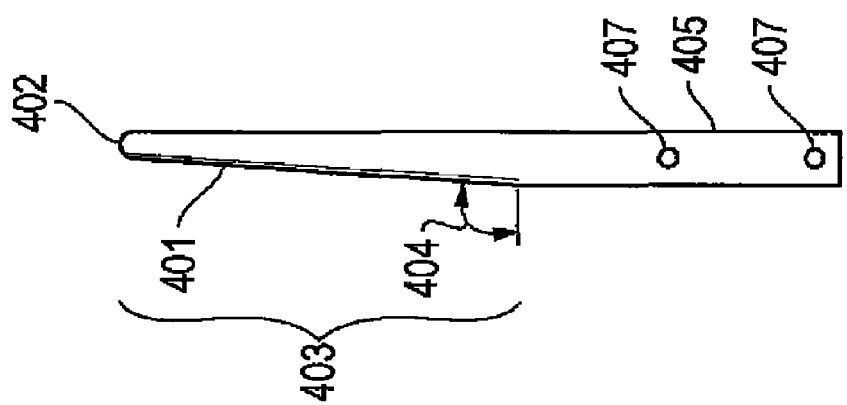
FIG. 4 is a view of a flat pattern of one embodiment of the blade portion of the device of the present invention.

With reference now to FIG. 4, a view of a flat pattern of one embodiment of the blade portion of the device of the present invention. More specifically, this view illustrates one embodiment of the length and the taper of the blade without showing the curvature of the blade. In this embodiment, the blade is sharpened 401 and begins to taper at a distance that is 81.13 millimeters 403 from the distal end of the blade 402. In this embodiment, the taper is shown to be a constant 93.63 degrees from an axis that is perpendicular to the length of the blade. The proximal end of the blade 405 is 10 millimeters in width 406 and contains holes 407 for use in securing the blade to a handle. The length, width, amount of taper, sharpness, and thickness of the blade can vary.

With reference now to FIG. 5, a view of a flat pattern of another embodiment of the blade portion of the device of the present invention. This view illustrates one embodiment of the length and the taper of the blade without showing the curvature of the blade.

With reference now to FIG. 6, a multi-perspective view of another embodiment of the blade portion of the device of the present invention is shown. In this embodiment, the proximal portion of the blade that is enclosed by the handle 602 contains two oval-shaped holes 601 for the purpose of fixing the handle to the blade. This embodiment also contains a transition portion 603 that is located between the junction 604 and the curved distal portion of the blade 605. In this embodiment, the junction 604 is shown to have a radius of 5.08 millimeters such that the inner angle of the junction as measured between the proximal portion of the blade 606 and the transition portion 603 is one hundred forty degrees (140°). The transition portion 603 is shown to be straight in this embodiment and 11.43 millimeters in length. The curved distal portion of the blade 605 is shown to have a radius of 12.7 millimeters. This embodiment also shows that blade thickness 607 to be 1.78 millimeters.

Figure 7:
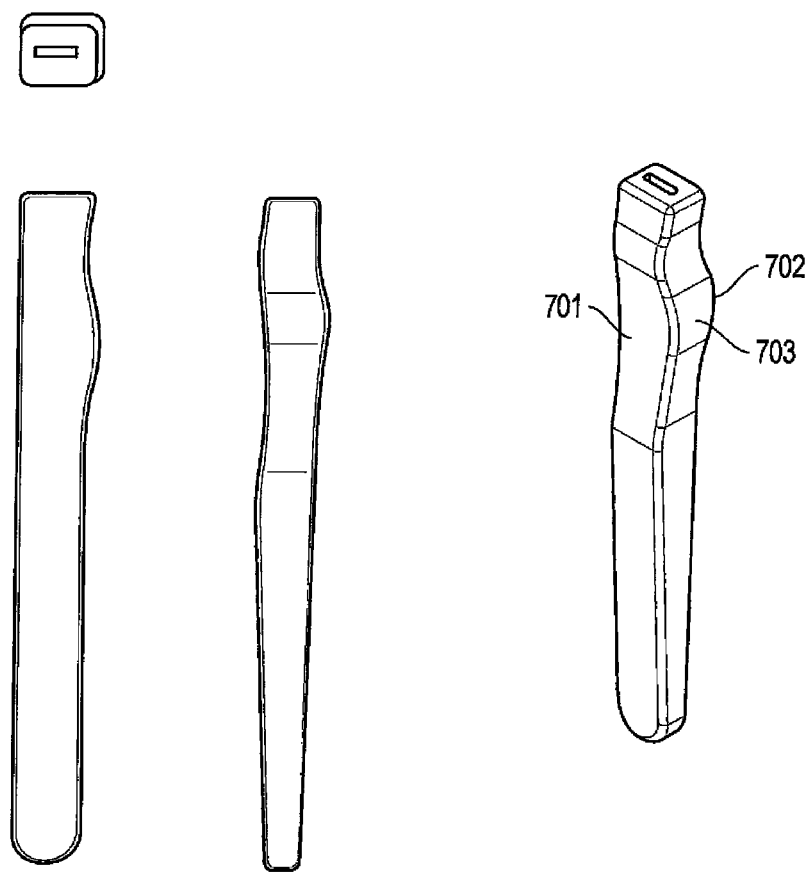
FIG. 7 is a multi-perspective view of another embodiment of the handle portion of the device of the present invention.

With reference now to FIG. 7, a multi-perspective view of another embodiment of the handle portion of the device of the present invention is shown. In this embodiment, the handle does not include a guard but the shape of the handle improves the user's ability to grip and manipulate the device. In particlar, three surfaces of the distal portion of the handle are rounded. One surface of the distal portion of the handle is rounded inward 701. In addition, two surfaces of the distal portion of the handle are rounded outward. First, the surface that is on the opposite side of the handle from the rounded-inward surface 701 is rounded outward 702. Second, one of the two remaining surfaces that are adjacent to the rounded-inward surface 701 is rounded outward 703.

Figure 8:
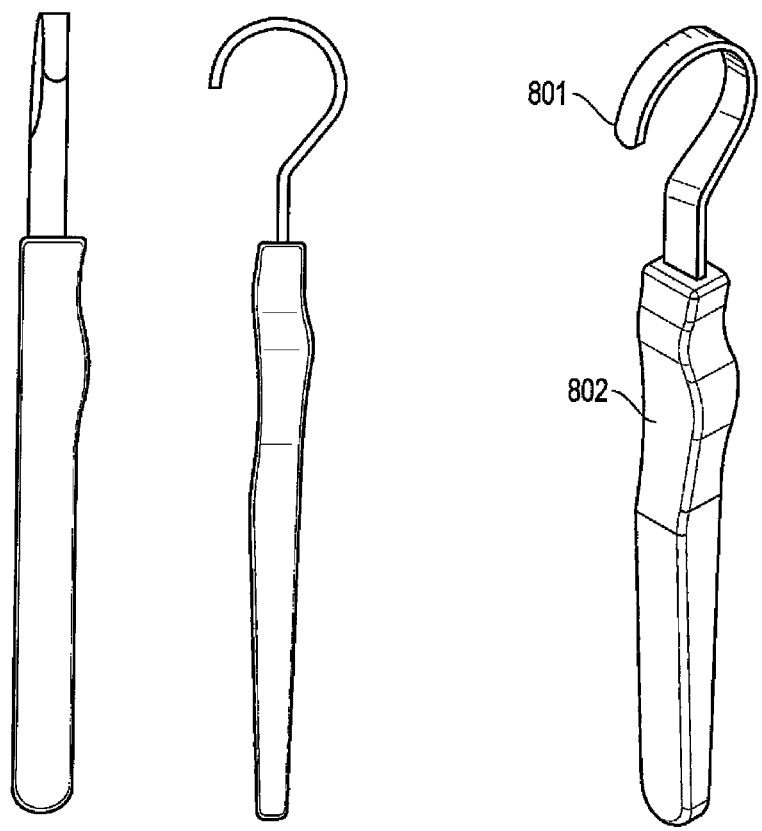
FIG. 8 is a multi-perspective view of another embodiment of the device of the present invention.

With reference now to FIG. 8, a multi-perspective view of another embodiment of the device of the present invention is shown. In this embodiment, the blade is connected to the handle such that the side of the handle that is rounded inward 802 is located on the same side of the device as the end of the distal portion of the blade 801.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A device for the removal of tissue comprising: a rigid blade for removal of tissue from a human or animal body, said rigid blade having a proximal portion affixed to a handle and being non-retractable with respect thereto an a distal portion with a blunt, non-cutting tip, wherein said distal portion of said blade is curved with one face of said distal portion forming the outer curve of said distal portion and wherein one edge of said distal portion of said blade is sharpened.

2. The device in claim 1 which further includes an elongated handle that is connected to said proximal portion of said blade.

3. The device in claim 1 which further includes a junction that is located between said proximal portion of said blade and said distal end of said blade wherein said junction curves in the opposite direction of said curve of said distal portion.

4. The device in claim 1 which further includes a guard that is connected to said proximal portion of said blade.

5. The device in claim 1 in which the width of said blade is tapered.

6. The device of claim 1 in which the full length of said edge of said blade is sharpened.

7. The device of claim 1 in which both edges of said distal portion are sharpened.

8. The device of claim 1 in which the full length of both edges of said blade are sharpened.

9. The device in claim 1 in which said curved portion forms approximately three-fourths of a circle.

10. A method for removing tissue from a body, comprising:
    inserting a rigid blade through an incision into a human or animal body, said rigid blade having a proximal portion affixed to a handle and being non-retractable with respect thereto and a distal portion with a blunt, non-cutting tip, wherein said distal portion of said blade is curved with one face of said distal portion forming the inner curve of said distal portion and the other face of said distal portion forming the outer curve of said distal portion and wherein one edge of said distal portion of said blade is sharpened;
    manipulating said blade so as to cut tissue within said body; and
    removing said blade through said incision.

11. The method in claim 10, which further includes an elongated handle that is connected to said proximal portion of said blade.

12. The method in claim 10, which further includes a junction that is located between said proximal portion of said blade and said distal end of said blade wherein said junction curves in the opposite direction of said curve of said distal portion.

13. The method in claim 10, which further includes a guard that is connected to said proximal portion of said blade.

14. The method in claim 10 in which the width of said blade is tapered.

15. The method in claim 10 in which the full length of said edge of said blade is sharpened.

16. The method in claim 10 in which both edges of said distal portion are sharpened.

17. The method in claim 10 in which the full length of both edges of said blade are sharpened.

18. The method in claim 10 in which said curved portion forms approximately three-fourths of a circle.

* * * * *